United States Patent [19]

Nedelec et al.

[11] 3,931,151
[45] Jan. 6, 1976

[54] DIBENZO (B,F) AZEPINES

[75] Inventors: Lucien Nedelec, Le Raincy; Jacques Guillaume, Aulnay-sous-Bois; Andre Allais, Les Lilas, all of France

[73] Assignee: Roussel-UCLAF, Paris, France

[22] Filed: Oct. 3, 1973

[21] Appl. No.: 403,108

[30] Foreign Application Priority Data
Oct. 9, 1972  France .................................. 72.35665

[52] U.S. Cl. ............................ 260/239 D; 424/244
[51] Int. Cl.² ...................................... C07D 223/26
[58] Field of Search .......................... 260/239 D

[56] References Cited
FOREIGN PATENTS OR APPLICATIONS

| | | | |
|---|---|---|---|
| 1,099,749 | 1/1968 | United Kingdom............. | 260/239 D |
| 1,000,192 | 8/1964 | United Kingdom............. | 260/239 D |
| 1,114,970 | 5/1968 | United Kingdom............. | 260/239 D |
| 442,317 | 8/1967 | Switzerland..................... | 260/239 D |

*Primary Examiner*—R. Gallagher
*Assistant Examiner*—D. B. Springer
*Attorney, Agent, or Firm*—Hammond & Littell

[57] ABSTRACT

Novel dibenzo (b,f) azepines of the formula

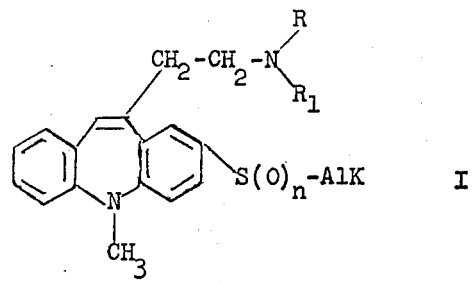

wherein R is alkyl of 1 to 4 carbon atoms, $R_1$ is selected from the group consisting of hydrogen and alkyl of 1 to 4 carbon atoms, n is 0, 1 or 2 and AlK is alkyl of 1 to 2 carbon atoms and their non-toxic, pharmaceutically acceptable acid addition salts having antidepressant and neurosedative activity.

6 Claims, No Drawings

DIBENZO (B,F) AZEPINES

STATE OF THE ART

French patent No. 2,043,486 describes dibenzo (b,f) azepines optionally substituted with halogen and French medical patent No. 6398 M describes dibenzo (b,f) azepines substituted in the 10-position with an amine chain with one carbon atom between the nitrogen atom and the 10-carbon of the dibenzo (b,f) azepine ring, and unsubstituted on the benzene rings.

OBJECTS OF THE INVENTION

It is an object of the invention to provide the novel dibenzoazepines of formula I and their acid addition salts.

It is another object of the invention to provide a novel process for the preparation of the compounds of formula I and novel intermediates produced therein.

It is a further object of the invention to provide novel antidepressant and neurosedative compositions and to provide a novel method of relieving depression in warm-blooded animals.

These and other objects and advantages of the invention will become obvious from the following detailed description.

The novel dibenzo (b,f) azepines of the invention are selected from the group consisting of compounds of the formula

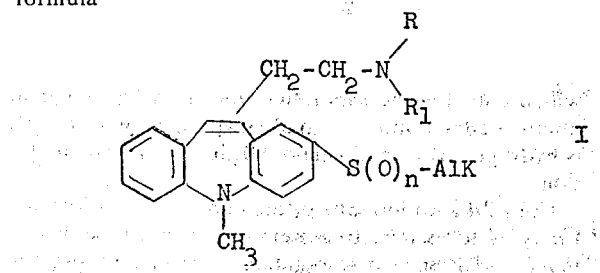

wherein R is alkyl of 1 to 4 carbon atoms, $R_1$ is selected from the group consisting of hydrogen and alkyl of 1 to 4 carbon atoms, n is 0, 1 or 2 and AlK is alkyl of 1 to 2 carbom atoms and their non-toxic, pharmaceutically acceptable acid addition salts.

Examples of suitable acids for the formation of the non-toxic, pharmaceutically acceptable acid addition salts of the compounds of formula I are inorganic acids such as hydrochloric acid, hydrobromic acid, nitric acid, sulfuric acid or phosphoric acid and organic acids such as acetic acid, formic acid, benzoic acid, maleic acid, fumaric acid, succinic acid, tartaric acid, citric acid, oxalic acid, benzylic acid, glyoxylic acid, aspartic acid, alkane sulfonic acids and arylsulfonic acids.

The preferred compounds of the invention of formula I are those wherein AlK is ethyl, n is 0 or 2 and R and $R_1$ have the above definitions and their non-toxic pharmaceutically acceptable acid addition salts.

The novel process of the invention for the preparation of the dibenzoazepines of formula I comprises reacting a compound of the formula

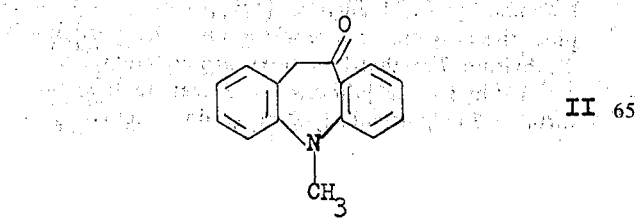

with N-bromosuccinimide in dimethylformamide to obtain the product of the formula

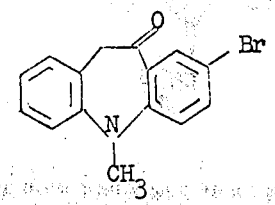

reacting the latter with an alkyl orthoformate of the formula $HC(OZ)_3$ wherein Z is lower alkyl of 1 to 7 carbon atoms to form a compound of the formula

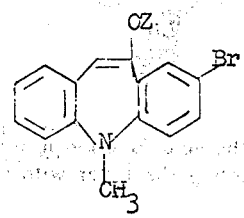

treating the latter with a cuprous alkylmercaptan of the formula Cu—S—AlK wherein AlK has the above definition followed then hydrolysing the resulting compound to obtain a compound of the formula

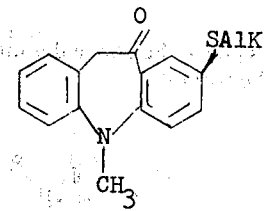

reacting the latter with an alkyl haloalkanoate of the formula

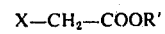

wherein X is chlorine, bromine or iodine and R′ is lower alkyl of 1 to 7 carbon atoms in the presence of zinc to form a compound of the formula

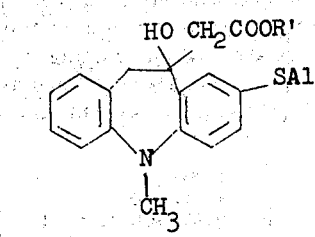

dehydrating the latter in an acid media to form an ester of the formula

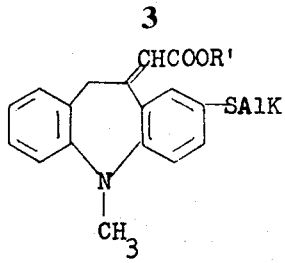

VIII

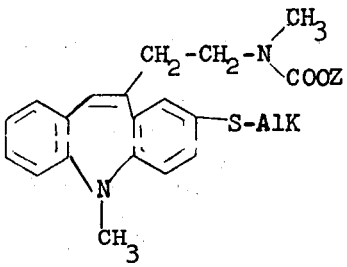

XII treating the latter with a saponification agent and then with an acid to form an acid of the formula

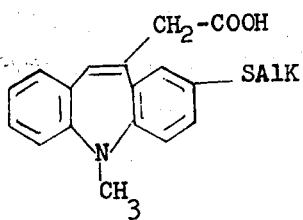

IX transforming the acid function into a functional derivative and reacting the latter with an amine of the formula

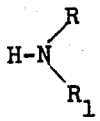

X wherein R and $R_1$ have the above definition to obtian a compound of the formula

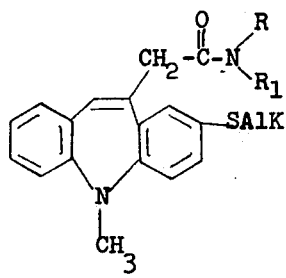

XI and reacting the latter with a mixed alkali metal hydride to obtain the corresponding compound of formula I wherein n is O and optionally reacting the latter with an oxidizing agent to obtain a compound of formula I wherein $n$ is 1 or 2 or reacting the product of formula I wherein $n$ is O, AlK is defined as above and R and $R_1$ are methyl with an alkyl chloroformate of the formula

wherein Z is alkyl of 1 to 7 carbon atoms to obtain a compound of the formula which can be saponified and decarboxylated to obtain a compound of formula I wherein R is methyl, $R_1$ is hydrogen, $n$ is O and AlK have the above definition or reacting the product of formula XII with a oxidizing agent to obtain a compound of the formula

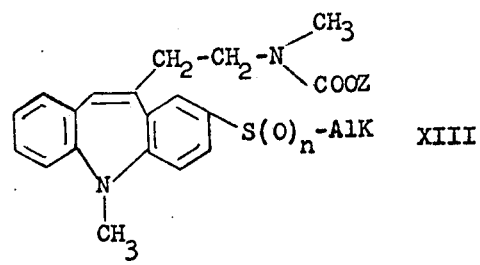

XIII which can then be saponified and decarboxylated to obtain a compound of formula I wherein $n$ is 1 or 2, $R_1$ is hydrogen, R is methyl and AlK has the above definition.

The acid addition salts of the compounds of formula I may be formed by treatment of the free base of formula I with the corresponding inorganic or organic acids without isolation of the free base, particularly with practically stoichiometric proportions.

Among the preferred conditions of the invention, the alkyl orthoformate is preferably methyl or ethyl orthoformate and in the alkyl haloalkanoate of formula VI X is chlorine or bromine such as ethyl chloroacetate or ethyl bromoacetate. The dehydration of the compound of formula VII is effected with a strong mineral acid or an arylsulfonic acid. The functional derivative of the compound of formula IX is preferably an aryl ester, i.e, phenyl substituted with p-nitro which can be obtained by reacting the acid of formula IX with p-nitrophenol in the presence of a dialkylcarbodiimide or a dicycloalkylcarbodiimide. The mixed alkali metal hydride is preferably lithium aluminum hydride and the oxidizing agent is preferably hydrogen peroxide.

The novel intermediates of the invention formed in the process are the products of formula V, particularly 2-ethylthio-5-methyl-10,11-dihydro [5H] dibenzo (b,f) azepine-11-one; the products of formula VII, particularly 2-ethylthio-5-methyl-11-hydroxy-11-ethoxycarbonylmethyl-10,11-dihydro [5H] dibenzo (b,f) azepine; the ethylenic esters of formula VIII, particularly 2-ethylthio-5-methyl-11-ethoxycarbonylmethylene-10,11-dihydro [5H] dibenzo (b,f) azepine; the acids of formula IX, particularly 2-ethylthio-5-methyl-11-carboxymethyl [5H] dibenzo (b,f) azepine; and the compounds of formula XI, particularly 2-ethylthio-5-methyl-11-(dimethylcarbamoylmethyl) [5H] dibenzo (b,f) azepine.

The novel antidepressant and neurosedative compositions of the invention are comprised of an effective amount of at least one compound of formula I or their non-toxic, pharmaceutically acceptable acid addition salts and a pharmaceutical carrier. The compositions may be in solid or liquid form such as tablets, dragees, gelules, granules, suppositories, or injectable solutions or suspensions prepared in the usual manner. The excipients may be any of those ordinarily used such as talc, gum arabic, lactose, amidon, magnesium stearate, cacao butter, aqueous or non-aqueous vehicles, animal or vegetable fatty bodies, paraffinic derivatives, glycols, preservatives, and diverse wetting agents, dispersants or emulsifiers.

The compositions are useful as antidepressant or neurosedative medicaments and are useful for the treatment of depressive states like anxiety.

The novel method of the invention for relieving depression in warm-blooded animals comprises administering to warmblooded animals an antidepressantly effective amount of at least one compound of formula I and their non-toxic, pharmaceutically acceptable acid addition salts. The compounds may be administered orally, rectally, or parenterally. The usual useful dose is 0.5 to 5 mg/kg depending upon the method of administration and the particular compound.

In the following examples there are described several preferred embodiments to illustrate the invention. However, it should be understood that the invention is not intended to be limited to the specific embodiments.

EXAMPLE 1

2-ethylthio-5-methyl-11-(β-dimethylaminoethyl) [5H] dibenzo (b,f) azepine and its hydrochloride

STEP A:

2-bromo-5-methyl-10,11-dihydro [5H] dibenzo (b,f) azepine-11-one 22.81 g of N-bromosuccimide were added over 15 minutes at room temperature to a solution of 25 g of 5-methyl-10,11-dihydro [5H] dibenzo (b,f) azepine-10-one in 250 ml of dimethylformamide under a nitrogen atmosphere and the mixture was stirred for 30 minutes at room temperature. The reaction mixture was poured into 2 liters of ice water and was extracted with ether. The ether extracts were washed with water, dried over magnesium sulfate and evaporated to dryness to obtain 34 g of 2-bromo-5-methyl-10,11-dihydro [5H] dibenzo (b,f) azepine-11-one. The product was dissolved in 100 ml of refluxing ethyl acetate and the solution was filtered hot and concentrated to the start of crystallization. The mixture was iced for 30 minutes and vacuum filtered. The recovered precipitate was washed with ethyl acetate and dried under reduced pressure to obtain 29.5 g of the said product in the form of pale yellow crystals melting at 128°–129°C.

| Analysis: | $C_{15}H_{12}BrNO$ | | | |
|---|---|---|---|---|
| Calculated: | %C 59.62 | %H 4.00 | %Br 26.44 | %N 4.63 |
| Found: | 59.3 | 3.8 | 26.1 | 4.5 |

STEP B:

2-bromo-5-methyl-11-ethoxy [5H] dibenzo (b,f) azepine

A suspension of 29.5 g of 2-bromo-5-methyl-10,11-dihydro [5H] dibenzo (b,f) azepine-11-one, 295 ml of ethanol and 29.5 ml of ethyl orthoformate was heated to 70°C and then 1 g of p-toluene sulfonic acid was added thereto in small fractions. The mixture was held at 70°C for 1½ hours and then 15 ml of triethylamine were added dropwise while still hot and the mixture was then cooled. The product crystallized and the mixture was diluted with 300 ml of distilled water, was stirred at room temperature for 30 minutes and was vacuum filtered. The recovered precipitate was washed with water and dried to obtain 31.8 g of 2-bromo-5-methyl-11-ethoxy [5H] dibenzo (b,f) azepine as pale yellow crystals melting at 131°C.

| Analysis: | $C_{17}H_{16}BrNO$ | | | |
|---|---|---|---|---|
| Calculated: | %C 61.83 | %H 4.88 | %Br 24.19 | %N 4.24 |
| Found: | 61.8 | 5.0 | 24.2 | 4.3 |

STEP C:

2-ethylthio-5-methyl-10,11-dihydro [5H] dibenzo (b,f) azepine-11-one

A mixture of 31.8 g of 2-bromo-5-methyl-11-ethoxy [5H] dibenzo (b,f) azepine, 17.85 g of cuprous ethylmercaptan, 320 ml of 99% quinoline and 48 ml of pyridine was refluxed for 5 hours and after cooling, the resulting solution was poured into 4 liters of 6N hydrochloric acid. The mixture was stirred for 30 minutes at room temperature and was then extracted with methylene chloride. The organic extracts were washed with 2N hydrochloric acid and then water until the wash waters were neutral. The solution was dried over magnesium sulfate and evaporated to dryness to obtain 30 g of product. The product was purified by chromatography over silica gel with a 9:1 benzene-ethyl acetate mixture as eluant which was evaporated to obtain 27.1 g of 2-ehtylthio-5-methyl-10,11-dihydro [5H] dibenzo (b,f) azepine-11-one as pale yellow crystals melting at 54°–55°C.

| Analysis: | $C_{17}H_{17}NOS$ | | | |
|---|---|---|---|---|
| Calculated: | %C 72.04 | %H 6.04 | %N 4.94 | %S 11.31 |
| Found: | 72.1 | 5.8 | 5.0 | 11.1 |

STEP D:

2-ethylthio-5-methyl-11-hydroxy-11-ethoxycarbonyl-methyl-10,11-dihydro [5H] dibenzo (b,f) azepine A complex of zinc and ethyl bromoacetate was prepared by reacting zinc and a solution of ethyl bromoacetate in methylal at reflux to obtain an 0.84M solution of zinc complex of ethyl bromoacetate. 300 ml of this solution were added over 20 minutes at 8–10°C to a solution of 22.7 g of 2-ethylthio-5-methyl-10,11-dihydro [5H] dibenzo (b,f) azepine -11-one in 290 ml of tetrahydrofuran and the mixture was stirred for 3 hours at 10°C and then maintained for 16 hours at 0°C. A solution of 120 g of ammonium chloride in 1.2 liters of distilled water was then added dropwise while keeping the temperature below 10°C and the mixture was extracted with methylene chloride. The organic phase was washed with water, dried over magnesium sulfate and distilled to dryness under reduced pressure to obtain 35 g of 2-ethylthio-5-methyl-11-hydroxy-11-ethoxycarbonylmethyl-10,11-dihydro [5H] dibenzo (b,f) azepine in the form of a yellow oil soluble in chlorinated solvents, alcohols and ethyl acetate and insoluble in water. The product was used as is for the next step.

I.R. Spectrum (chloroform): Presence of aromatic at 1602, 1588 $cm^{-1}$, of OH at 3476 $cm^{-1}$ and of carbonyl at 1712 $cm^{-1}$.

| U.V. Spectrum (ethanol): | | |
|---|---|---|
| Max. at 280 nm | $E_{1cm}^{1\%} = 442$ | $\epsilon = 16,400$ |
| Max. at 380 nm | $E_{1cm}^{1\%} = 6$ | |

| U.V. Spectrum (ethanol): | | |
|---|---|---|
| Max. at 272-273nm | $E_{1cm}^{1\%} = 685$ | $\epsilon = 24,600$ |
| Inflex. towards 292nm | $E_{1cm}^{1\%} = 520$ | |
| Max. at 384nm | $E_{1cm}^{1\%} = 186$ | $\epsilon = 6,700$ |

STEP F:

2-ethylthio-5-methyl-11-carboxymethyl [5H] dibenzo (b,f) azepine

A mixture of 27.3 g of 2-ethylthio-5-methyl-11-ethoxycarbonylmethylene-10,11-dihydro [5H] dibenzo (b,f) azepine in 750 ml of ethanol was stirred until complete dissolution occured and then 120 g of potassium hydroxide were added. The mixture was held at room temperature for 30 minutes and then was poured into a mixture of 2 kg of ice and 270 ml of hydrochloric acid. The mixture was stirred for 30 minutes and was extracted with methylene chloride. The organic phase was washed with water, dried over magnesium sulfate and distilled to dryness under reduced pressure. The 23 g of product were dissolved in 200 ml of refluxing ethyl acetate and the solution was filtered and was slightly concentrated. Crystallization was induced and the mixture was iced for 30 minutes and then vacuum filtered. The recovered precipitate was washed with ethyl acetate and dried under reduced pressure to obtain 19.64 g of 2-ethylthio-5-methyl-11 -carboxymethyl [5H] dibenzo (b,f) azepine which was used as is for the next step. For analysis, the product was crystallized from ethyl acetate and was a yellow crystalline solid melting at 164°C.

| Analysis: | $C_{19}H_{19}NO_2S$ | | | |
|---|---|---|---|---|
| Calculated: | %C 70.12 | %H 5.88 | %N 4.03 | %S 9.85 |
| Found: | 69.9 | 6.0 | 4.1 | 9.5 |

STEP E:

2-ethylthio-5-methyl-11-ethoxycarbonylmethylene-10,11-dihydro [5H] dibenzo (b,f) azepine A mixture of 35 g of 2-ethylthio-5-methyl-11-hydroxy-11-ethoxycarbonylmethyl-10,11-dihydro [5H] dibenzo (b,f) azepine, 500 ml of ethanol and 50 ml of 2N hydrochloric acid was stirred for 3 hours at room temperature. The mixture was poured into 2 kg of ice and the mixture was extracted with ethyl acetate. The organic extracts were washed with water, dried over magnesium sulfate and distilled to dryness under reduced pressure. The residue was chromatographed over silica gel with a 98-2 mixture of benzene-ethyl acetate as eluant which was evaporated to obtain 27.3 g of 2-ethylthio-5-methyl-11-ethoxycarbonylmethylene-10,11-dihydro [5H] dibenzo (b,f) azepine in the form of a yellow oil soluble in alcohol, chlorinated solvents and ethyl acetate and insoluble in water.

I.R. Spectrum (chloroform): Absence of OH, presence of carbonyl at 1699 $cm^{-1}$

STEP G:

2-ethylthio-5-methyl-11-(p-nitrophenoxycarbonyl) methyl [5H] dibenzo (b,f) azepine A suspension of 2 g of 2-ethylthio-5-methyl-11-carboxymethyl [5H] dibenzo (b,f) azepine in 40 ml of ethyl acetate was heated until dissolution occured and after cooling the mixture, 840 mg of p-nitrophenol were added thereto. After total dissolution, 1.28 g of dicyclohexylcarbodiimide in 4.8 ml of ethyl acetate were added thereto and the mixture was refluxed with stirring for 1 hour. 130 mg of dicyclohexylcarbodiimide were then added and reflux with stirring was continued for 30 minutes. After cooling, the mixture was vacuum filtered and the filtrate was distilled to dryness under reduced pressure to obtain 3.9 g of raw product. The product was purified by chromatography over silica gel with a 98-2 benzene-ethyl acetate mixture as eluant to obtain 2.4 g of 2-ethylthio-5-methyl-11-(p-nitrophenoxycarbonyl)-methyl [5H] dibenzo (b,f) azepine as a yellow oil soluble in ethyl acetate, ethanol and chloroform and insoluble in water.

I.R. Spectrum (chloroform): Presence of C=O at 1763 $cm^{-1}$, of aromatic and conjugated C=C at 1618, 1594, 1575 and 1488$^{cm-1}$ and $NO_2$ at 1522 and 1347$^{cm-1}$ U.V. Spectrum (ethanol)
Max. at 263 nm    $E_{1cm}^{1\%} = 860$    $\epsilon = 38,400$

STEP H:

2-ethylthio-5-methyl-11-dimethylcarbamoylmethyl [5H] dibenzo (b,f) azepine

A mixture of 11.35 g of 2-ethylthio-5-methyl-11-(p-nitrophenoxycarbonyl)methyl [5H] dibenzo (b,f) azepine in 45 ml of chloroform was stirred until dissolution occured and a solution of 12 ml of dimethylamine in 45 ml of chloroform was added dropwise thereto in 10 minutes. The mixture was stirred for 1 hour at room temperature and then was poured into 250 ml of ice and water. The organic phase was recovered by decanting and was washed with water, dried over magnesium sulfate and distilled to dryness under reduced pressure to obtain 9 g of 2-ethylthio-5-methyl-11-dimethylcarbamoylmethyl [5H] dibenzo (b,f) azepine which was used as is for the next step. The product occured as a yellow oil soluble in chloroform, ethanol and ethyl acetate and insoluble in water.

I.R. Spectrum (chloroform): Presence of amide: complex band at 1643, 1634$^{cm-1}$, and aromatic and C=C at 1597, 1561 and 1578$^{cm-1}$.

U.V. Spectrum (ethanol):
Inflex. towards 219 nm    $E_{1cm}^{1\%} = 692$
Max. at 261 nm            $E_{1cm}^{1\%} = 888$    $\epsilon = 31,200$
Inflex. towards 343nm     $E_{1cm}^{1\%} = 24$

STEP I:

2-ethylthio-5-methyl-11-($\beta$-dimethylaminoethyl) [5H] dibenzo (b,f) azepine and its hydrochloride 2.2 g of lithium aluminum hydride were added in small fractions to a solution of 9 g of 2-ethylthio-5-methyl-11-dimethylcarbamoylmethyl [5H] dibenzo (b,f) azepine in 270 ml of tetrahydrofuran while keeping the temperature below 30°C and the mixture was stirred for 2 hours at room temperature and was cooled to 0°C. Ethyl acetate was added to the mixture followed by a 2N sodium hydroxide solution to dissociate the precipitate formed. The insolubles were removed by filtration and the organic phase was recovered by decanting. The aqueous phase was extracted with ethyl acetate and the combined organic phases were washed with water, dried over magnesium sulfate and evaporated to dryness. The residue was chromatographed over silica gel with a 60-30-10 mixture of cyclohexane-chloroform-triethylamine as eluant which was evaporated to obtain 7.1 g of raw 2-ethylthio-5-methyl-11-($\beta$-dimethylamino ethyl) [5H] dibenzo (b,f) azepine.

The product was dissolved in 200 ml of ethyl acetate and a solution of ethyl acetate saturated with hydrochloric acid was added dropwise thereto until the pH became acidic. The precipitate formed was dissolved in 200 ml of methylene chloride and 200 ml of ethyl acetate were added thereto. The methylene chloride was removed by distillation and the solution was filtered and concentrated to about 200 ml of ethyl acetate. Crystallization was induced and after icing, the mixture was vacuum filtered. The recovered precipitate was washed with ethyl acetate and dried under reduced pressure to obtain 5.85 g of a product melting at 176°C. Two successive crystallizations from ethyl acetate gave 4.05 g of 2-ethylthio-5-methyl-11-($\beta$-dimethylaminoethyl) [5H] dibenzo (b,f) azepine hydrochloride melting at 176°C. The product occured as yellow crystals soluble in chloroform, ethanol and water and slightly soluble in ethyl acetate.

| Analysis: | $C_{21}H_{27}ClN_2S$ | | | | |
|---|---|---|---|---|---|
| Calculated: | %C 67.26 | %H 7.25 | %N 7.47 | %S 8.55 | %Cl 9.45 |
| Found: | 67.0 | 7.0 | 7.2 | 8.8 | 9.5 |

EXAMPLE 2

2-ethylsulfonyl-5-methyl-11-($\beta$-dimethylaminoethyl) [5H] dibenzo (b,f) azepine and its hydrochloride 5.1 ml of 30% hydrogen peroxide were added dropwise in 10 minutes to a solution of 4.25 g of 2-ethylthio-5-methyl-11-($\beta$-dimethylaminoethyl) [5H] dibenzo (b,f) azepine hydrochloride in 42.5 ml of acetic acid heated to 65°C and the mixture was stirred at 65°C for 4 hours and then was cooled. The mixture was poured into 200 ml of ice and water and the solution was made alkaline by addition of sodium hydroxide. The mixture was extracted with methylene chloride and the organic phase was washed with water, dried over magnesium sulfate and distilled to dryness under reduced pressure. The residue was chromatographed over silica gel with a 95-5 mixture of chloroform-methanol as eluant which was distilled to obtain 2.85 g of 2-ethylsulfonyl-5-methyl-11-($\beta$-dimethylaminoethyl) [5H] dibenzo (b,f) azepine.

The said product was dissolved in 50 ml of isopropanol and a solution of isopropanol saturated with gaseous hydrochloric acid was added dropwise until the pH was acidic. The resulting precipitate was redissolved by heating and the solution was filtered. The filtrate was concentrated to about 25 ml, was iced and vacuum filtered. The recovered product was washed with isopropanol and dried under reduced pressure to obtain 2.1 g of 2-ethylsulfonyl-5-methyl-11-($\beta$-dimethylaminoethyl) [5H] dibenzo (b,f) azepine hydrochloride which after it was crystallized from isopropanol melted at 206°C. The product occured as white crystals soluble in ethanol, chloroform and water and slightly soluble in ethyl acetate and isopropanol.

| Analysis: | $C_{21}H_{27}ClN_2O_2S$ | | | | |
|---|---|---|---|---|---|
| Calculated: | %C 61.98 | %H 6.69 | %N 6.88 | %S 7.88 | %Cl 8.71 |
| Found: | 61.9 | 7.0 | 6.9 | 7.8 | 8.4 |

EXAMPLE 3

2-ethylthio-5-methyl-11-(β-methylaminoethyl) [5H] dibenzo (b,f) azepine and its fumarate.

STEP A:

2-ethylthio-5-methyl-11-(β-methylaminoethyl)-N-ethoxycarbonyl [5H] dibenzo (b,f) azepine 4.5 ml of ethyl chloroformate were added dropwise to a solution of 4.5 g of 2-ethylthio-5-methyl-11-(β-dimethylaminoethyl) [5H] dibenzo (b,f) azepine (Example 1) in 45 ml of benzene and the mixture was refluxed for 5 hours and then was cooled. The mixture was poured into water and ice and was extracted with ethyl acetate. The organic extracts were washed with water, with 2N hydrochloric acid, again with water, dried over magnesium sulfate and distilled to dryness under reduced pressure to obtain 5.2 g of 2-ethylthio-5-methyl-11-(β-methyaminoethyl)-N-ethoxycarbonyl [5H] dibenzo (b,f) azepine which was used as is for the next step. The product occured as a yellow oil soluble in chloroform, ethanol and ethyl acetate and insoluble in water.

I.R. Spectrum (chloroform): Presence of complex carbonyl band towards $1691^{cm-1}$ and of aromatic at $1595^{cm-1}$ and $1577^{cm-1}$.

| U.V. Spectrum (ethanol): | | |
|---|---|---|
| Inflex. at 220 nm | $E_{1cm}^{1\%} = 531$ | |
| Max. at 262 nm | $E_{1cm}^{1\%} = 755$ | $\epsilon = 30,000$ |
| Inflex. at 344 nm | $E_{1cm}^{1\%} = 22$ | |

STEP B:

2-ethylthio-5-methyl-11-(β-methylaminoethyl) [5H] dibenzo (b,f) azepine and its fumarate.

4 g of potassium hydroxide were added to a solution of 4 g of 2-ethylthio-5-methyl-11-(β-methylaminoethyl)-N-ethoxycarbonyl [5H] dibenzo (b,f) azepine in 40 ml of 1N of n-butanol and the mixture was refluxed for 20 hours and then was cooled. The mixture was poured into ice and water and was extracted with ether. The ether extracts were washed with water and extracted with 2N hydrochloric acid to remove the amine fraction. The mixture was then made alkaline by addition of sodium hydroxide and extracted again with ether. The ether phase was washed with water, dried over magnesium sulfate and distilled to dryness under reduced pressure to obtain 2.84 g of raw 2-ethylthio-5-methyl-11-(β-methylaminoethyl) [5H] dibenzo (b,f) azepine.

The said 2.84 g were dissolved in 10 ml of methanol and then a solution of 950 mg of fumaric acid in 10 ml of methanol were added thereto. After dissolution, 50 ml of ethyl acetate were added and the mixture was filtered. The filtrate was concentrated and ethyl acetate was added until the appearance of a slight turbidity. Crystallization was inducted and the mixture was iced and vacuum filtered. The recovered precipitate was washed with ethyl acetate and dried under reduced pressure to obtain 3.25 g of raw product which was crystallized from isopropanol to obtain 2.78 g of the fumarate of 2-ethylthio-5-methyl-11-(β-methylaminoethyl) [5H] dibenzo (b,f) azepine in the form of pale yellow crystals melting at 135°C. The product was soluble in ethanol and water and slightly soluble in isopropanol.

| Analysis: | $C_{24}H_{28}N_2O_4S$ | | | |
|---|---|---|---|---|
| Calculated: | %C 65.43 | %H 6.40 | %N 6.35 | %S 7.28 |
| Found: | 65.1 | 6.2 | 6.2 | 7.3 |

EXAMPLE 4

2-ethylsulfonyl-5-methyl-11-(β-methylaminoethyl) [5H] dibenzo (b,f) azepine

STEP A:

2-ethylsulfonyl-5-methyl-11-(β-methylaminoethyl)-N-ethoxycarbonyl [5H] dibenzo (b,f) azepine A solution of 8.4 g of 2-ethylthio-5-methyl-11-(β-methylaminoethyl)-N-ethoxycarbonyl [5H] dibenezo (b,f) azepine (Example 3, Step A) in 84 ml of acetic acid was heated to 65°C and then 6.7 ml of 30% of hydrogen peroxide were added dropwise in 5 minutes. The mixture was held at 65°C for 5 hours and then was cooled and poured into an ice-water mixture. The mixture was extracted with ethyl acetate and the organic phase was washed with water, then with an aqueous solution saturated with sodium bicarbonate and then with water until the wash waters were neutral. The solution was dried over magnesium sulfate and distilled to dryness under reduced pressure. The residue was chromatographed over silica gel with a 60-30-10 cyclohexane-chloroform-triethylamine mixture as eluant which was distilled to obtain 6.95 g of 2-ethylsulfonyl-5-methyl-11-(β-methylaminoethyl)-N-ethoxycarbonyl [5H] dibenzo (b,f) azepine in the form of a yellow resin soluble in chloroform, ethanol and ethyl acetate.

I.R. Spectrum (chloroform): Presence of complexed carbonyl at 1689 and $1684^{cm-1}$, of aromatic and C=C at 1590, 1576 and $1566^{cm-1}$.

| U.V. Spectrum (ethanol): | | |
|---|---|---|
| Max. at 227 nm | $E_{1cm}^{1\%} = 520$ | $\epsilon = 22,300$ |
| Max. at 270 nm | $E_{1cm}^{1\%} = 580$ | $\epsilon = 24,800$ |
| Inflex. at 308 nm | $E_{1cm}^{1\%} = 63$ | |

STEP B:

2-ethylsulfonyl-5-methyl-11-(β-methylaminoethyl) [5H] dibenzo, (b,f) azepine 9.65 g of potassium hydroxide were added to a solution of 9.65 g of the product of Step A in 96.5 ml of 1N n-butanol and the mixture was refluxed for 20 hours, then cooled. The mixture was poured into ice and water and was extracted with ether. The ether extracts were washed with water and extracted with 2N hydrochloric acid to remove the amine fraction. The mixture was made alkaline with sodium hydroxide addition and was extracted with ether. The extracts were washed with water, dried over magnesium sulfate and distilled to dryness under reduced pressure to obtain 6.8 g of raw product. The latter was chromatographed over silica gel using a 60-30-10 chloroform-acetone-triethylamine mixture as eluant which was distilled. The residue was chromatographed a second time using a 90-5-5 chloroform-methanol-triethylamine mixture as eluant which was distilled to obtain 4.6 g of 2-ethylsulfonyl-5-methyl-11-($\beta$-methylaminoethyl) [5H] dibenzo (b,f) azepine in the form of a yellow resin soluble in chlorinated solvents, alcohols, ethyl acetate, ether and dilute hydrochloric acid and insoluble in water.

| Analysis: | $C_{20}H_{24}N_2O_2S$ | | | |
|---|---|---|---|---|
| Calculated: | %C 67.39 | %H 6.79 | %N 7.86 | %S 8.99 |
| Found: | 67.2 | 6.6 | 7.7 | 8.7 |

I.R. Spectrum (chloroform): Presence of $SO_2$ at 1310 and 1145 $cm^{-1}$, of aromatic and C=C at 1182, 1569, 1560 and 1471 $cm^{-1}$, presence of NH and absence of C=O. U.V. Spectrum (ethanol):

Max. at 226 nm    $E_{1cm}^{1\%} = 742$    $\epsilon = 26,500$
Max. at 268 nm    $E_{1cm}^{1\%} = 788$    $\epsilon = 28,000$
Inflex. at 302 nm    $E_{1cm}^{1\%} = 96$

EXAMPLE 5

Tablets were prepared containing 50 mg of 2-ethylsulfonyl-5-methyl-11-($\beta$-methylaminoethyl) [5H] dibenzo (b,f) azepine and an excipient of lactose, talc, amidon and magnesium stearate.

PHARMACOLOGICAL DATA

A. Antidepressive activity against reserpine

The antidepressive activity was determined in this test by the antagonism exercised by the test compounds against the depressive effect of reserpine measured by the eyelid ptosis test codified by Rubin [J. Pharm. Exp. Ther., Vol. 120 (1957), p. 125]. The eyelid ptosis test is used to permit a quantitative evaluation of the state of the animal but the antagonism is equally exercised by all the neurodepressive symptoms of reserpine; immobility, adynamia, hypothermia, myosis, etc. The readings were taken every hour for 6 hours after an intraperitoneal injection of 1 mg/kg of reserpine to a group of rats which had received intraperitoneally one hour before varying doses of the test products. The ptosis provoked by the reserpine injection is attenuated by the previous injection of the test products more as the dose increased. The results of Table I are expressed as percent of protection as compared to the controls receiving ony reserpine.

TABLE I

| Products | % of protection | | | | |
|---|---|---|---|---|---|
| | 1 mg /kg | 2 mg /kg | 5 mg /kg | 10 mg /kg | 20 mg /kg |
| Hydrochloride of 2-ethyl-thio-5-methyl-11-($\beta$-dimethy- | | | | | |

TABLE I-continued

| Products | % of protection | | | | |
|---|---|---|---|---|---|
| | 1 mg /kg | 2 mg /kg | 5 mg /kg | 10 mg /kg | 20 mg /kg |
| lamino-ethyl) [5H] dibenzo (b,f) azepine (Product A) | | 9 | 46 | 46 | |
| Fumarate of 2-ethylthio-5-methyl-11-($\beta$-methylaminoethyl) [5H] dibenzo (b,f) azepine (Product C) | 6 | 31 | 62 | 56 | 59 |
| 2-Ethylsulfonyl-5-methyl-11-($\beta$-methylaminoethyl) [5H] dibenzo (b,f) azepine (Product D) | 31 | 48 | 76 | 86 | 75 |

Table I shows that the dose that reduced the eyelid ptosis provoked by reserpine by 50% ($DA_{50}$) was 4 mg/kg for product C and 2 mg/kg for product D.

B. Antitetrabenazine test

Tetrabenazine produces a depressive effect characterized by eyelid ptosis and a certain catatonic state and the previous administration of an antidepressant antagonises, hinders, retards or diminishes these symptoms. Groups of female rats weighing about 100-110 g received intraperitoneally the test products in aqueous solution at different doses and one hour later, received intraperitoneally 10 mg/kg of tetrabenazine. The animals were examined ½, 1, 1½ and 2 hours after the tetrabenazine injection. Each animal was checked for passive eyelid ptosis and catatonic state and the total values for each group was obtained in 4 tests. The results of Table II are expressed as a percentage of protection.

TABLE II

| Products | Doses in mg/kg | % of protection Ptose |
|---|---|---|
| Product A | 0.5 | 28 |
| | 1 | 70 |
| | 2 | 83 |
| | 5 | 89 |
| | 10 | 91 |
| | 20 | 88 |
| Hydrochloride of 2-ethyl-sulfonyl-5-methyl-11-($\beta$-dimethylaminoethyl) [5H]dibenzo (b,f) azepine (Product B) | 1 | 25 |
| | 2 | 39 |
| | 5 | 54 |
| | 10 | 60 |
| | 20 | 60 |
| Product C | 1 | 15 |
| | 2 | 53 |
| | 5 | 81 |
| | 10 | 76 |
| | 20 | 94 |
| Product D | 1 | 38 |
| | 2 | 58 |
| | 5 | 99 |
| | 10 | 88 |
| | 20 | 83 |

The results of Table II show that against ptosis, the $DA_{50}$ dose of product A was 0.75 mg/kg, of product B was less than 5 mg/kg, of product C was less than 2 mg/kg and of product D was less 2 mg/kg.

C. Potentialization of sleeping time

The potentialization of sleeping time was determined in a test with amytal [5-ethyl-5-isoamyl-barbituric acid] with groups of female mice weighing between 18 to 22 g. kept at 25°C for the duration of the test. The test products were administered intraperitoneally at different doses, one hour before an intravenous injection of 80 mg/kg of amytal. The time of sleep was noted as the time during which the refluxes of redress of the mice was negative and the average sleeping time in minutes for the groups was determined. The results are in Table III.

TABLE III

| Lots | Doses in mg/kg | Average sleeping time in minutes |
| --- | --- | --- |
| Controls | 0 | 35.4 |
| Product A | 5 | 44.9 |
|  | 10 | 42.8 |
|  | 20 | 56.5 |
| Controls | 0 | 35.4 |
| Product C | 5 | 39.8 |
|  | 10 | 46.9 |
|  | 20 | 57.8 |
|  | 50 | 108.4 |

Table III shows that the products tested potentialize the sleeping time provoked by amytal.

D. Acute toxicity

The acute toxicity was determined on mice of the Rockland strain weighing about 20 g which received intraperitoneally increasing doses of the test product. The animals were observed for 7 days and the average lethal dose ($DL_{50}$) was determined graphically by the method of Tainter el al. The $DL_{50}$ for product A was 100 mg/kg and 150 mg/kg for products B, C and D.

Various modifications of the products and methods of the invention may be made without departing from the spirit or scope thereof and it is to be understood that the invention is intended to be limited only as defined in the appended claims.

We claim:
1. A compound selected from the group consisting of a compound of the formula

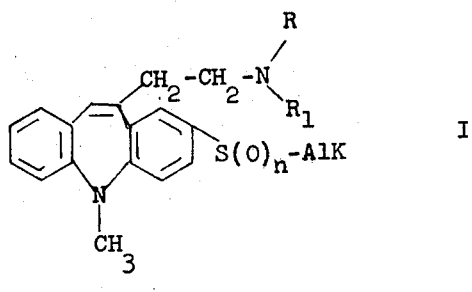

wherein R is alkyl of 1 to 4 carbon atoms, R is selected from the group consisting of hydrogen and alkyl of 1 to 4 carbon atoms, $n$ is 0 or 2 and AlK is alkyl of 1 to 2 carbon atoms and their non-toxic, pharmaceutically acceptable acid addition salts.

2. A compound of claim 1 wherein AlK is ethyl and $n$ is 0 or 2.

3. A compound of claim 1 selected from the group consisting of 2-ethylthio-5-methyl-11-(β-dimethylaminoethyl) [5H] dibenzo (b,f) azepine and its hydrochloride.

4. A compound of claim 1 selected from the group consisting of 2-ethylsulfonyl-5-methyl-11-(β-dimethylaminoethyl) [5H] dibenzo (b,f) azepine and its hydrochloride.

5. A compound of claim 1 selected from the group consisting of 2-ethylthio-5-methyl-11-(β-methylaminoethyl) [5H] dibenzo (b,f) azepine and its fumarate.

6. A compound of claim 1 which is 2-ethylsulfonyl-5-methyl-11-(β-methylaminoethyl) [5H] dibenzo (b,f) azepine.

* * * * *